United States Patent [19]

Nowacki et al.

[11] Patent Number: 4,715,376

[45] Date of Patent: Dec. 29, 1987

[54] ISOLATION OF GAS IN HYDRAULIC SPARK GAP SHOCK WAVE GENERATOR

[75] Inventors: Christopher Nowacki, Arlington Heights; Alfred G. Brisson, Kildeer, both of Ill.

[73] Assignee: Trutek Research, Inc., Lake Zurich, Ill.

[21] Appl. No.: 928,805

[22] Filed: Nov. 7, 1986

[51] Int. Cl.[4] .................... A61B 17/22

[52] U.S. Cl. .................... 128/328; 367/147; 128/24 A

[58] Field of Search .................... 128/328, 24 A, 660; 367/147, 145; 181/106, 118, 120

[56] References Cited

U.S. PATENT DOCUMENTS 3,970,076 7/1976 Hepp et al. .................... 128/24.5

4,630,607 12/1986 Duinker et al. .................... 128/328

FOREIGN PATENT DOCUMENTS 90138 10/1983 European Pat. Off. .................... 128/328

*Primary Examiner*—Michael H. Thaler

*Attorney, Agent, or Firm*—Robert M. Wolters

[57] ABSTRACT

Apparatus for generating shock waves for destruction of kidney stones comprises an upwardly opening ellipsoidal reflector. A resilient diaphragm closes the otherwise open end of the reflector, and the reflector is filled with water or other suitable liquid. A spark gap is provided in the reflector at the first focus point thereof, and the reflector is positioned relative to a human body such that the diaphragm presses against the body and the second focus point of the ellipsoid lies precisely on a kidney stone to be destroyed. Electronic apparatus is provided for causing a repeating spark across the gap to generate a series of shock waves which are focused by the ellipsoidal reflector to concentrate on a kidney stone. Gas is released by the sparks, and either a small tube surrounds the spark gap, or a diaphragm immediately overlies the spark gap to isolate water adjacent the spark gap from most of the water in the reflector. The isolated water is constantly recirculated to flush away gas.

2 Claims, 3 Drawing Figures

ISOLATION OF GAS IN HYDRAULIC SPARK GAP SHOCK WAVE GENERATOR

RELATED APPLICATION

This application relates to the same subject matter as our copending application Ser. No. 928,524, filed Nov. 7, 1986 for Degassification of Water in Hydraulic Spark Gap Shock Wave Generator.

BACKGROUND OF THE INVENTION

Kidney stones, and also naturally-occurring stones in the bladder and the ureter can be exquisitely painful, and often require surgical relief. Excision or destruction of stones in the bladder and sometimes in the ureter can be relatively easily accomplished, but removal of stones from the kidney is a major procedure.

Removal of stones from the kidney is a very serious and traumatic surgical procedure. A large incision is made in the body. The kidney is essentially removed from the body and cut open. The stone or stones are then removed, whereupon the kidney is sutured and returned to the body, with the body then being sutured. Various efforts have been made to destroy or disintegrate kidney stones so that they can be excreted with the urine.

Chemotherapy is available as a non-invasive therapy for uric acid stones. In this therapy, the urine is alkalyzed, and the stone is dissolved over a substantial period of time. This requires detection of the stone before an acute phase is reached.

The next step was the use of ultrasound or an electrohydraulic shock wave produced by discharging a capacitor across a spark gap under water or other suitable liquid. Early efforts required invasion of the body, either through the urethra or through a surgical incision.

Subsequently, efforts have been made for the extracorporeal destruction of kidney stones through the use of a focused shock wave. In U.S. Pat. No. 3,942,531, for example, a reflector is used which is a portion of an ellipsoid. The spark gap is located at the first focus point of the ellipsoid, and the ellipsoid is positioned relative to the body so that the kidney stone or other calculus or concretion is at the second focus point of the ellipsoid. The reflector is filled with water. Discharge of a spark across the gap causes rapid vaporization of a portion of the water, and resultant generation of a shock wave which is focused by the reflector on the kidney stone. The shock wave travels through the water in the ellipsoidal reflector, and through the human tissues to the kidney stone. A repetition of the spark gap shock wave generation over a period of perhaps an hour, is necessary to destroy a kidney stone.

Repeated shock wave generation as just described results in an accumulation of gas within the water in the reflector. It has been found that the best approach to the human body is to have the patient lie on his back with the ellipsoidal reflector below him. This results in collection of gas at the interface between the water in the reflector and the body of the patient This materially reduces energy transfer from the shock wave generator to the human body, and inhibits destruction of a kidney stone.

Simply replacing the water in the reflector has little effect in removing the gas, which tends to remain as an air bubble at the top of the reflector and beneath the diaphragm. This problem is exacerbated by a tendency of the gas to adhere to the underside of a diaphragm.

OBJECTS AND SUMMARY OF THE INVENTION

It is an object of the present invention to preclude the introduction of or generation of gas into the water filling a reflector in which a shock wave is generated by discharge of a spark across a spark gap.

More specifically, it is an object of the present invention to provide for shock wave generation by discharge of a spark across a spark gap in a reflector filled with water or the like wherein the spark gap is isolated from most of the water in the reflector so that gas generated by spark discharge is isolated from most of the water in the reflector and is readily removed.

In accordance with the present invention we provide an upwardly directed, truncated ellipsoidal reflector having the upper end covered with a flexible diaphragm of elastomeric of plastic resin material. The reflector is filled with water. A spark gap is provided at the first focus point of the reflector, and a spark generated across the gap causes vaporization of water to generate a shock wave. In accordance with one embodiment of the present invention, the spark gap structure including the gap is surrounded by a thin wall cylindrical tube through which fresh water is constantly circulated. Gas released from the water by spark generation thus is continually flushed out of the tube, and is totally isolated from most of the water in the ellipsoidal reflector. In accordance with a second embodiment of the present invention, a thin diaphragm is disposed above the spark gap structure, thereby isolating the apex portion of the ellipsoidal reflector. A constant flow of fresh water through the isolated portion of the reflector removes gas from the vicinity of the spark gap mechanism. Gas is totally isolated from the major portion of the water in the reflector.

THE DRAWINGS

The present invention will best be understood from the following specification when taken in connection with the accompanying drawings wherein.

DETAILED DISCLOSURE OF THE ILLUSTRATED EMBODIMENTS

Figure 1:
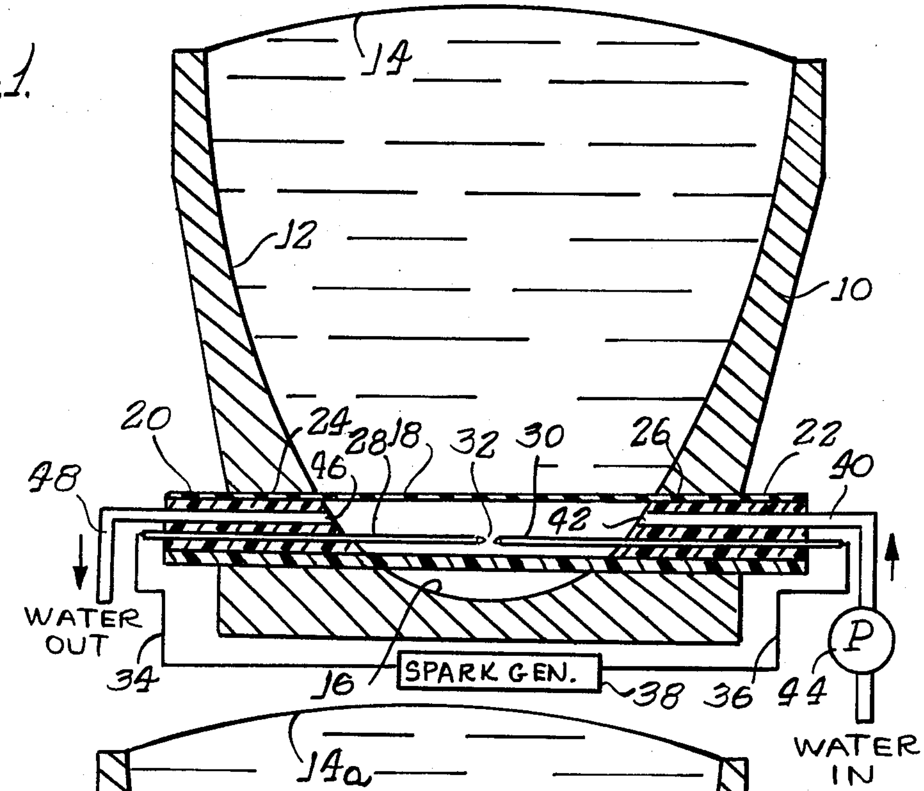
FIG. 1 is a longitudinal sectional view of the structure incorporating the first embodiment of the present invention.

Turning now in greater particularity to the drawings, and first to FIG. 1, there will be seen a metal base or block 10 having a hollow interior in the form of a truncated ellipsoidal reflector 12. A flexible diaphragm 14 is secured across the open top of the reflector 12 by any suitable means (not shown). The diaphragm is waterproof as well as flexible, and preferably is made of an elastomeric or plastic resin material. The apex 16 of the reflector is at the bottom thereof, and it is intended that the upwardly opening reflector should be positioned beneath a patient with the diaphragm 14 pressing across the patient's back. This allows ready access to the kidneys, and specifically permits positioning of the second focus point (not shown) of the reflector precisely at the kidney stone to be destroyed. The reflector 12 is completely filled with water, and causes the diaphragm 14 to bulge upwardly slightly as shown.

A thin-walled plastic tube 18 extends through the base 10 transversely of the axis of the reflector 12 and includes the first focus point of the ellipsoid as will be mentioned shortly hereinafter. Plastic or other insulating plugs 20 and 22 are provided at the opposite ends of the tube 18 and wedge the tube in corresponding bores 24 and 26 in the body 10.

Electrodes 28 and 30 extend longitudinally through the blocks 20 and 22 and longitudinally through the tube 18 to close proximity to one another, defining a spark gap 32 therebetween. The electrodes extend outwardly from the plugs 20 and 22 and are connected by means such as wires 34 and 36 to a spark generator 38.

A pipe or conduit 40 extends into a bore 42 in the plug 22, and a pump 44 in the pipe 40 circulates water into the tube 18. A complementary bore 46 exhausts water from the tube 18 into a drain pipe 48. Water is thus circulated constantly through the tube 18. The tube may be rather limp and is of such a thin wall construction that it might tend to sag, except that the water pressure inside thereof maintains a positive pressure that holds the tube in the erect position shown.

The spark gap generator is provided with suitable controls (not shown) to charge and discharge a condenser to cause a repetition of sparks across the spark gap 32. The spark causes an instantaneous flashing of water in the gap into steam, and thereby generates a shock wave at the first focal point of the ellipsoidal reflector 12. The shock waves so generated are focused by the reflector on the kidney stone in the patient, and in due course the kidney stone is reduced to granules or dust which are carried out by the urine without invasion of the patient's body. The repeating spark causes a certain amount of gas to be released, which in accordance with the teachings of the prior are would have risen to the underwide of the diaphragm 14, thereby producing an interface that would be a poor transferer of energy. In accordance with the present teachings, the gas that is generated is immediately flushed out of the tube 18 by the constant flow of water therethrough. The thin wall of the tube 18 is very resilient and does not interfere in any significant way with transfer of the energy from the spark gap to the kidney stone.

Figure 2:
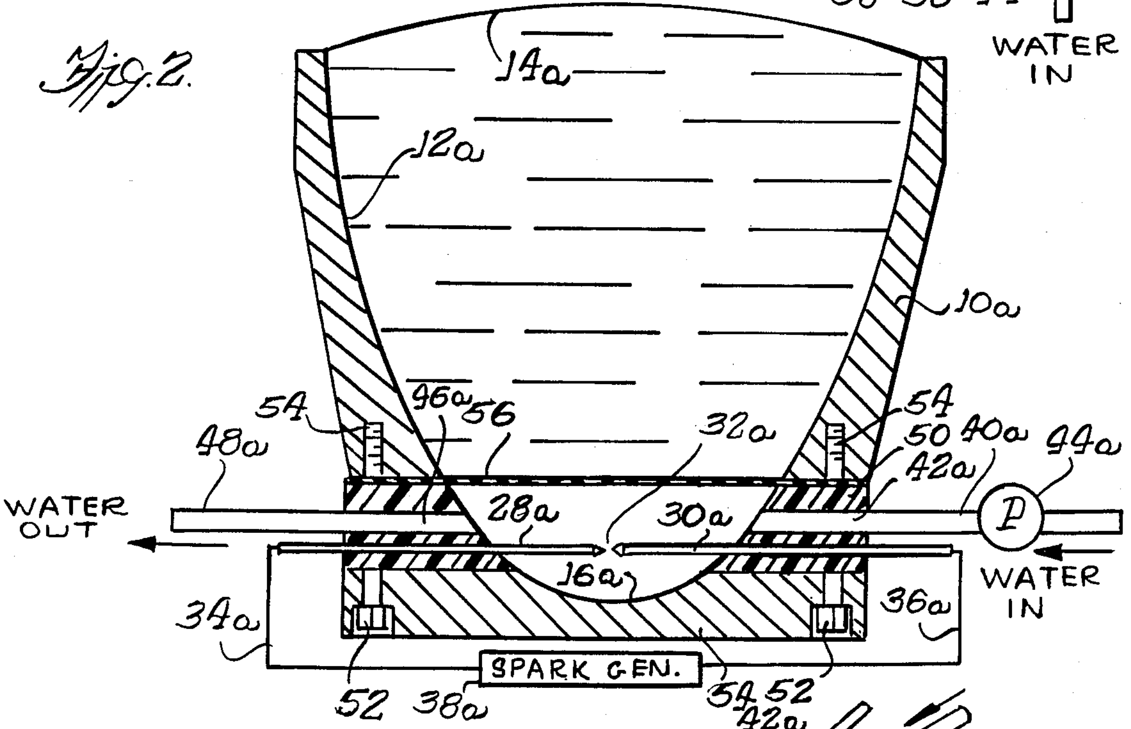
FIG. 2 is a view similar to FIG. 1 showing the second embodiment of the present invention.
Figure 3:
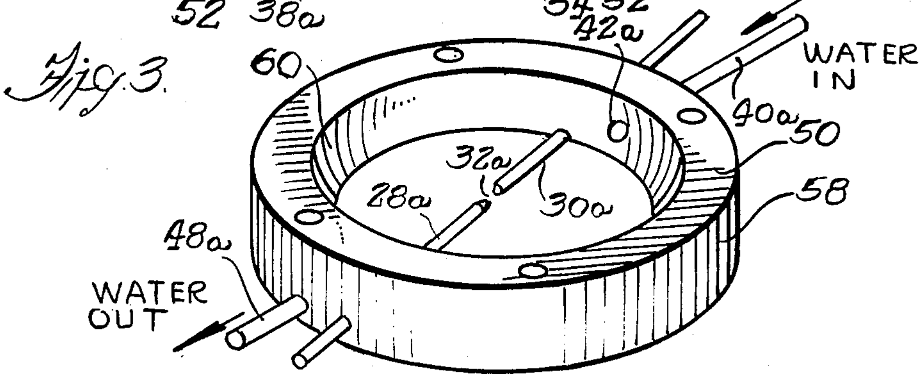
FIG. 3 is a perspective view of a portion of the structure of FIG. 2.

A modification of the invention is shown in FIGS. 2 and 3. Many of the parts remain as disclosed heretofore, and similar numerals are used for such parts with the addition of the suffix a. A horizontal slice is removed from the base or body 10*a* upwardly a short distance from the apex 16*a*. An insulating ring 50 replaces said slice. Bolts 52 extend up through the bottom 54 of the body, through the ring 50, and are threaded into tapped apertures 54 in the upper portion of the body. A very thin diaphragm 56 extends across the top of the ring and is clamped against the underside of the upper portion of the body by the ring. The outer surface of the ring 50 is conveniently cylindrical as at 58, whereas the inner surface 60 is tapered so as to form a continuation of the surface of the ellipsoidal reflector 12*a*, whereby not to interfere with the aiming of the shock wave.

The water supply conduits 42*a* and 46*a* extend substantially diametrically through the ring, as do the electrodes 28*a* and 30*a* defining the spark gap 32*a* at the first focus point of the ellipsoidal reflector 12*a*. The diaphragm 56 is sufficiently thin and is made of an elastomeric or plastic resin material as to be rather limp, and is sustained in horizontal position by a slightly greater water pressure below the diaphragm than above it. Gas released by reiterating spark in the gap 32*a* cannot rise above the diaphragm 56, and is flushed out by the water constantly flowing through the lower portion of the ellipsoidal reflector beneath the diaphragm 56. Consequently, it is not possible for any gas to rise into the water in the major portion of the ellipsoidal reflector and to collect beneath the diaphragm 14*a*.

In accordance with the present invention, gas generated by a repeating spark in a spark gap to generate a shock wave is prevented from moving very far from the spark gap, and specifically is prevented from rising into the water in the ellipsoidal reflector above the spark gap. A constant flow of fresh water flushes such gas out of the space adjacent the spark gap, either in a small tube or beneath a diaphragm spaced only a short distance above the spark gap. Provision of the tube or of the isolating diaphragm does not significantly interfere with the amount of energy transferred from the spark gap to the kidney stone at the second focus point of the ellipsoidal reflector.

The specific embodiments of the invention as herein shown and described are for illustrative purposes only. Various changes in structure will no doubt occur to those skilled in the art, and will be understood as forming a part of the present invention.

The invention is claimed as follows:

1. Apparatus for generating shock waves comprising a reflector open at one end, a resilient diaphram across the open end of the reflector, said reflector having a liquid such as water therein, means providing a spark gap in said reflector, a spark across said gap generating a shock wave and producing gas in said liquid, isolation means within said reflector closely adjacent to said spark gap means isolating said spark gap means from most of the liquid in said reflector and having a volume of not more than substantially 25% of the volume of said reflector, a liquid such as water being retained about said spark gap means by said isolation means, and means for removing from said isolation means gas formed as an incident to discharging a spark across said spark gap, said diaphram being adapted to be pressed against a living body, and the liquid retained by said isolation means and in said reflector coupling said shock wave through said diaphram to said living body, said reflector being upwardly opening and having a vertical axis of rotation, said isolation means comprising a substantially straight tube transverse of and intersecting said axis, said means for removing gas from said isolation means comprising means for flowing the liquid retained by said isolation means in one end of said tube and out the other.

2. Apparatus for generating shock waves comprising a reflector open at one end, a resilient diaphram across the open end of the reflector, said reflector having a liquid such as water therein, means providing a spark gap in said reflector, a spark across said gap generating a shock wave and producing gas in said liquid, isolation means within said reflector closely adjacent to said spark gap means isolating said spark gap means from most of the liquid in said reflector and having a volume of not more than substantially 25% of the volume of said reflector, a liquid such as water being retained about said spark gap means by said isolation means, and means for removing from said isolation means gas formed as an incident to discharging a spark across said spark gap, said diaphram being adapted to be pressed against a living body, and the liquid retained by said isolation means and in said reflector coupling said shock wave through said diaphram to said living body, wherein said isolation means comprising a diaphram, and further including a ring inserted in said base and having an inner surface shaped as a continuation of said reflector, said diaphram being disposed over an upper surface of said ring and clamped thereby, said ring supporting said spark gap means substantially diametrically of said reflector and of said ring, and said means for removing gas compising liquid conduit means extending through said ring on one side for flowing liquid into said reflector below said isolation means diaphram and liquid conduit means diametrically disposed relative to said first mentioned liquid conduit means on the other side of said ring for flowing liquid out of said relector beneath said isolation means diaphram.

* * * * *